(12) United States Patent
Susak et al.

(10) Patent No.: US 9,095,543 B2
(45) Date of Patent: Aug. 4, 2015

(54) COSMETIC COMPOSITIONS COMPRISING CYANODIPHENYLACRYLATES

(75) Inventors: Milanka Susak, North York (CA); Ismail Ahmed Syed, Glen Oaks, NY (US); Linda Josephine Najdek, East Islip, NY (US); Mirela Cristina Ionita-Manzatu, Old Bethpage, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 13/266,578

(22) PCT Filed: Apr. 28, 2010

(86) PCT No.: PCT/US2010/032677
§ 371 (c)(1),
(2), (4) Date: Feb. 6, 2012

(87) PCT Pub. No.: WO2010/129313
PCT Pub. Date: Nov. 11, 2010

(65) Prior Publication Data
US 2012/0189676 A1    Jul. 26, 2012

Related U.S. Application Data

(60) Provisional application No. 61/175,222, filed on May 4, 2009.

(51) Int. Cl.
*A61K 31/12* (2006.01)
*A61K 8/40* (2006.01)
*A61K 8/893* (2006.01)
*A61K 8/894* (2006.01)
*A61Q 19/00* (2006.01)
*A61Q 1/02* (2006.01)
*A61Q 1/06* (2006.01)
*A61Q 1/10* (2006.01)
*A61Q 17/04* (2006.01)

(52) U.S. Cl.
CPC . *A61K 31/12* (2013.01); *A61K 8/40* (2013.01); *A61K 8/893* (2013.01); *A61K 8/894* (2013.01); *A61Q 19/00* (2013.01); *A61Q 1/02* (2013.01); *A61Q 1/06* (2013.01); *A61Q 1/10* (2013.01); *A61Q 17/04* (2013.01)

(58) Field of Classification Search
CPC ......... A61K 31/12; A61K 8/40; A61K 8/894; A61Q 17/04
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,677,152 A | 6/1987 | Allen et al. | |
| 4,702,844 A | 10/1987 | Flesher et al. | |
| 4,803,067 A | 2/1989 | Brunetta et al. | |
| 4,889,845 A | 12/1989 | Ritter et al. | |
| 4,970,252 A | 11/1990 | Sakuta et al. | |
| 5,077,211 A | 12/1991 | Yarosh | |
| 5,118,496 A | 6/1992 | Herstein | |
| 5,183,588 A | 2/1993 | Salerno et al. | |
| 5,183,589 A | 2/1993 | Brunetta et al. | |
| 5,190,762 A | 3/1993 | Yarosh | |
| 5,236,986 A | 8/1993 | Skauta | |
| 5,272,079 A | 12/1993 | Yarosh | |
| 5,296,231 A | 3/1994 | Yarosh | |
| 5,412,004 A | 5/1995 | Tachibana et al. | |
| 5,576,354 A | 11/1996 | Deflandre et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |
| 5,914,101 A | 6/1999 | Tapley et al. | |
| 5,928,629 A | 7/1999 | Allard et al. | |
| 5,955,091 A | 9/1999 | Hansenne | |
| 5,989,528 A | 11/1999 | Tanner et al. | |
| 6,146,617 A | 11/2000 | Kurz et al. | |
| 6,146,649 A | 11/2000 | Hansenne | |
| 6,342,209 B1 | 1/2002 | Patil et al. | |
| 6,776,980 B1 | 8/2004 | Allard et al. | |
| 6,936,241 B2 | 8/2005 | Yamada et al. | |
| 6,964,773 B1 | 11/2005 | Morrison | |
| 7,083,800 B1 * | 8/2006 | Terren et al. | 424/401 |
| 7,166,275 B2 | 1/2007 | Bertz et al. | |
| 7,357,919 B2 | 4/2008 | Candau | |
| 7,368,105 B2 | 5/2008 | Candau | |
| 7,666,442 B2 * | 2/2010 | Morariu | 424/401 |

(Continued)

FOREIGN PATENT DOCUMENTS

| CA | 2642783 | 9/2007 |
|---|---|---|
| EP | 1 153 600 | 11/2001 |

(Continued)

OTHER PUBLICATIONS

Saint Louis, C. "Confused by SPF? Take a Number" May 14, 2009. The New York Times.*
Bonda, Craig; Research Pathways to Photostable Sunscreens; Cosmetic & Toiletries®; The International Magazine of Cosmetic Technology; Innovation Through Interaction; vol. 123; No. 2; www.CosmeticsandToiletries.com; Feb. 2008. (11 submitted pages).
PCT International Search Report; International Application No. PCT/US2010/033328; Completion Date: Dec. 14, 2010; Date of Mailing: Dec. 14, 2010.

(Continued)

*Primary Examiner* — Sean Basquill
*Assistant Examiner* — Andrew S Rosenthal
(74) *Attorney, Agent, or Firm* — Julie Blackburn

(57) ABSTRACT

A topical composition comprising at least one α-cyanodiphenylacrylate and dimethicone silylate.

18 Claims, No Drawings

(56) References Cited

U.S. PATENT DOCUMENTS

| | | |
|---|---|---|
| 8,075,808 B2 | 12/2011 | Bonda et al. |
| 8,088,364 B2 * | 1/2012 | Breyfogle et al. ............ 424/59 |
| 2001/0028888 A1 | 10/2001 | Heidenfelder et al. |
| 2002/0086042 A1 | 7/2002 | Delrieu et al. |
| 2003/0228339 A1 | 12/2003 | El-Nokaly et al. |
| 2005/0019280 A1 | 1/2005 | Bertz et al. |
| 2005/0186153 A1 | 8/2005 | Bonda et al. |
| 2006/0034875 A1 | 2/2006 | Nakanishi et al. |
| 2006/0078514 A1 | 4/2006 | Bertz et al. |
| 2006/0147505 A1 | 7/2006 | Tanzer et al. |
| 2006/0280712 A1 | 12/2006 | Kuroda et al. |
| 2007/0207113 A1 | 9/2007 | Joerger et al. |
| 2009/0039322 A1 | 2/2009 | Bonda et al. |
| 2009/0039323 A1 * | 2/2009 | Bonda et al. ............ 252/589 |
| 2009/0041847 A1 | 2/2009 | Bonda et al. |
| 2009/0042312 A1 | 2/2009 | Bonda |
| 2009/0057627 A1 | 3/2009 | Bonda et al. |
| 2009/0074687 A1 | 3/2009 | Bonda et al. |
| 2009/0155371 A1 | 6/2009 | Sojka et al. |

FOREIGN PATENT DOCUMENTS

| | | |
|---|---|---|
| EP | 1 213 006 | 6/2002 |
| EP | 1819315 | 8/2007 |
| EP | 2 025 324 | 2/2009 |
| JP | 61-018708 | 1/1986 |
| JP | 11-514670 | 12/1999 |
| JP | 2000-026262 | 1/2000 |
| JP | 2000-191490 | 7/2000 |
| JP | 2001-240525 | 9/2001 |
| JP | 3658561 | 6/2005 |
| JP | 2007-145859 | 6/2007 |
| KR | 20000022115 | 4/2000 |
| WO | WO98/50000 | 11/1998 |
| WO | WO2004/024798 | 3/2004 |
| WO | WO2005/009341 | 2/2005 |
| WO | WO2006/087066 | 8/2006 |
| WO | WO2007/133769 | 11/2007 |
| WO | WO2009/020676 | 2/2009 |

OTHER PUBLICATIONS

PCT Written Opinion of the International Searching Authority, or the Declaration; International Application No. PCT/US2010/033328; Completion Date: Dec. 14, 2010; Mailing Date: Dec. 14, 2010.

PCT International Search Report; International Application No. PCT/US2010/032677; Completion Date: Jan. 19, 2011; Date of Mailing: Jan. 21, 2011.

PCT Written Opinion of the International Searching Authority, or the Declaration; International Application No. PCT/US2010/032677; Completion Date: Jan. 19, 2011; Mailing Date: Jan. 21, 2011.

PCT International Search Report; International Application No. PCT/US2010/032683; Completion Date: Jan. 19, 2011; Date of Mailing: Jan. 21, 2011.

PCT Written Opinion of the International Searching Authority, or the Declaration; International Application No. PCT/US2010/032683; Completion Date: Jan. 19, 2011; Mailing Date: Jan. 21, 2011.

PCT International Search Report; International Application No. PCT/US2010/032692; Completion Date: Dec. 14, 2010; Date of Mailing: Jan. 3, 2011.

PCT Written Opinion of the International Searching Authority, or The Declaration; International Application No. PCT/US2010/032692; Completion Date: Dec. 14, 2010; Mailing Date: Jan. 3, 2011.

PCT International Search Report; International Application No. PCT/US2010/032702; Completion Date: Dec. 15, 2010; Date of Mailing: Jan. 3, 2011.

PCT Written Opinion of the International Searching Authority, or The Declaration; International Application No. PCT/US2010/032702; Completion Date: Dec. 15, 2010; Mailing Date: Jan. 3, 2011.

Supplementary European Search Report; Applic. No. EP10772631.7; Completion Date: Aug. 23, 2012; Date of Mailing: Aug. 31, 2012.

Newton, et al.; Silicone Technology Offers Novel Methods for Delivering Active Ingredients; SOFW Journal; 130(5); pp. 8-13; Downloaded from : http://www3.dowcorning.com/content/publishedlit/27-1153-01.pdf on Oct. 23, 2013.

* cited by examiner

COSMETIC COMPOSITIONS COMPRISING CYANODIPHENYLACRYLATES

CROSS-REFERENCE TO RELATED APPLICATIONS

The present application is a national stage filing of PCT/US2010/032677, filed Apr. 28, 2010, which claims priority of U.S. Provisional Application No. 61/175,222 filed on May 4, 2009.

TECHNICAL FIELD

The invention is in the field of compositions for application to keratinous surfaces for coloring, conditioning, or treating the keratinous surface for improvement.

BACKGROUND OF THE INVENTION

There are many problems in formulating topical compositions. In order to be commercially acceptable, the composition must be stable. No matter how efficacious a product is, the product will not be commercially acceptable if it separates or otherwise deteriorates under normal shipping and storage conditions prior to sale. In addition, when compositions applied to the skin are meant to form a film, it is important that the film formed be relatively homogeneous on the skin. One criterion for assessing the adequacy of a film formed on skin is spreadability, which means that when a composition is applied to skin it should spread onto the skin to form a relatively even film. This is particularly important when it comes to color cosmetics and sunscreens. Obviously a sun bather does not want to apply a sunscreen film that leaves gaps in coverage, nor does a consumer want to apply a lipstick that does not evenly color the lips. It is believed that spreadability and relatively homogeneous film formation on skin is improved when the composition is formulated with ingredients that improve dispersibility of various components such as particulates, oils, and polymers, in the composition.

Cyanodiphenylacrylates are generally known for enhancing SPF when incorporated into sunscreens. U.S. Patent Publication 2009/0039323A1 teaches that certain α-cyanodiphenylacrylates act by accepting the triplet excited state energy generated by organic sunscreens such as Avobenzone when it is exposed to certain environmental conditions. The end result is that the excess energy formed by the unstable Avobenzone is then dissipated and does not result in an unstable ingredient that compromises the stability of the formula. However, cosmetic formulators must combine more than cyanodiphenylacrylates and organic sunscreens to make a commercially acceptable cosmetic formula, particularly when it may contain other ingredients. One formulation concern is aesthetics. No matter how efficacious a product is, consumers will not buy it if it is aesthetically unpleasant when applied to skin. In order to improve aesthetics, cosmetic formulators use light, dry oils such as silicones. Silicones provide aesthetically pleasing cosmetic formulas but contribute to certain disadvantages when it comes to film formation on skin. In particular, cosmetics containing silicone may provide uneven film formation on skin surfaces. This is an obvious disadvantage when formulating products such as sunscreens, where an even film on skin is desired.

It has been found that in addition to its SPF enhancing capability, certain α-cyanodiphenylacrylates, despite their lipophilic character, are excellent dispersants for cosmetic ingredients, including those that are polar or that may contain both lipophilic and hydrophilic moieties. The combination of α-cyanodiphenylacrylates with oxyalkylenated organosiloxanes is particularly effective in forming topical cosmetic products that provide a spreadable, smooth and even film when applied to skin. Most unexpectedly, the α-cyanodiphenylacrylates are compatible with both silicones and organosiloxane emulsifiers, enabling formation of composition that provide a smooth and even film on skin where the ingredients present are dispersed in the composition. When dispersion of cosmetic ingredients is optimized the composition exhibits maximum effectiveness in forming a film on skin, improving SPF protection, and providing commercially acceptable aesthetics.

SUMMARY OF THE INVENTION

The invention is directed to a topical composition comprising at least one α-cyanodiphenylacrylate and at least one oxyalkylenated organosiloxane emulsifier.

The invention is also directed to a method for stabilizing a composition comprising formulating said composition at least one α-cyanodiphenylacrylate and at least one oxyalkylenated organosiloxane emulsifier.

DETAILED DESCRIPTION

The compositions of the invention are topical. They may be in the aqueous solution or suspension, emulsion, or anhydrous form. They may be in the form of liquids, solids, or semi-solids at room temperature (e.g. 25° C.).

I. The α-Cyanodiphenylacrylate

The composition of the invention comprises at least one α-Cyanodiphenylacrylate. Suggested amounts range from about 0.001 to 60%, preferably from about 0.005 to 50%, more preferably from about 0.01 to 45%, with all percentages mentioned herein percentages by weight unless otherwise indicated.

Preferred is where the α-Cyanodiphenylacrylate is as disclosed in U.S. Patent Publication No. 2009/0039323A1, hereby incorporated by reference in its entirety. The α-Cyanodiphenylacrylate may have the general formula:

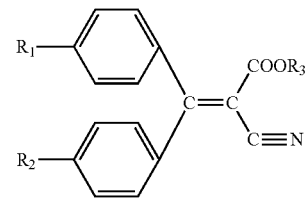

wherein $R_1$ and $R_2$ are each independently straight or branched chain $C_{1-30}$ alkoxy; any non-alkoxy $R_1$ or $R_2$ radical is hydrogen; and $R_3$ is a straight or branched chain $C_{1-30}$ alkyl.

Preferred is wherein $R_1$ and $R_2$ are each independently $C_{1-8}$, and any non-alkoxy radical $R_1$ or $R_2$ is hydrogen; and $R_3$ is a straight of branched chain $C_{2-20}$ alkyl.

More preferred is wherein $R_1$ and $R_2$ are each independently methoxy, and any non-methoxy $R_1$ or $R_2$ is hydrogen; and $R_3$ is a $C_{2-20}$ alkyl.

Most preferred is wherein the α-cyanodiphenylacrylate is ethylhexylmethoxycrylene, or 2-ethylhexyl 2-cyano-3-(4-methoxyphenyl)-3-phenylpropenoate, a liquid that may be purchased from Hallstar Company under trade name RX-14180.

II. The Oxyalkylenated Organosiloxane Emulsifier

The oxyalkylenated organosiloxane emulsifier used in the compositions of the invention may be present in amounts ranging from about 0.001 to 50%, preferably from about 0.005 to 40%, more preferably from about 0.01 to 35%. Suitable emulsifiers may be in the liquid, solid, or semi-solid form, and may be linear or crosslinked. The organosiloxane emulsifier may be linear or crosslinked.

One type of emulsifier that may be used is generically referred to as dimethicone copolyol or alkyl (e.g. cetyl) dimethicone copolyol. It may have a Hydrophile/Lipophile Balance (HLB) ranging from about 2 to 18. Preferably it is nonionic, having an HLB ranging from about 2 to 12, preferably about 2 to 10, most preferably about 4 to 6.

One type of suitable emulsifier has the general formula:

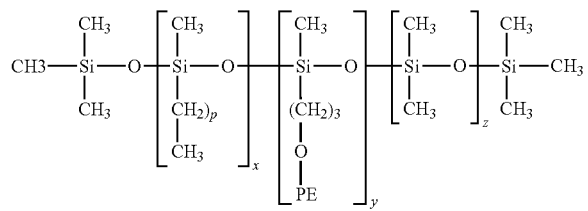

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x, y, and z are each independently ranging from 0 to 1 million with the proviso that x and y cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol. One type of silicone surfactant is wherein p is such that the long chain alkyl is cetyl or lauryl, and the surfactant is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

Another type of organosiloxane emulsifier has the general formula:

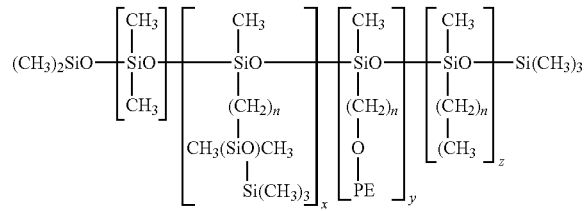

wherein each n is independently 0-100 with the proviso that there must be at least one PE radical. More preferred is where each n independently ranges from about 2 to 30, and PE $(-C_2H_4O)_a-(-C_3H_6O)_b-H$ wherein a is 0 to 25, b is 0-25 with the proviso that both a and b cannot simultaneously be 0; and wherein x, y, and z are each independently 0 to 1,000,000 with the proviso that there is at least one PE. More preferred is where the ingredient is Lauryl PEG-9 Polydimethylsiloxyethyl Dimethicone Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Elastomers are generally prepared by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference in their entirety.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also excellent emulsification properties.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; PEG-15 Laurylpolydimethylsiloxyethyl Crosspolymer; and mixtures thereof.

In one preferred embodiment, the composition comprises from about 0.1 to 25% of the linear organosiloxane emulsifier and from about 0.1 to 25% of the crosslinked organosiloxane emulsifier.

III. Other Ingredients

The compositions of the invention may comprise other ingredients including but not limited to those further set forth herein.

A. Oils

In the event the compositions of the invention are in anhydrous or emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

1. Volatile Oils

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin. Volatile oils are more desirable when the skin care products containing the cyanodiphenylacrylate are being formulated for consumers that have combination or oily skin, or for indications where a heavy, greasy film on skin is undesirable.

(a). Volatile Silicones

Cyclic silicones are one type of volatile silicone that may be used in the composition. Such silicones have the general formula:

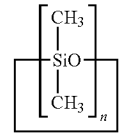

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

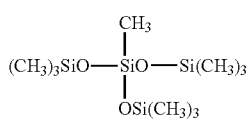

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(ii). Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

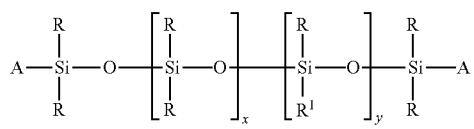

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

(e). Fluorinated Oils

Various types of fluorinated oils may also be suitable for use in the compositions including but not limited to fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

C. Aqueous Phase Structuring Agents

In the case where the compositions are in the form of aqueous solutions, dispersions or emulsions, in addition to water the aqueous phase may contain one or more aqueous phase structuring agents, that is, an agent that increases the viscosity or thickens, the aqueous phase of the composition. This is particularly desirable when the composition is in the form of a serum or gel. The aqueous phase structuring agent should be compatible with the cyanodiphenylacrylate particularly if the particular cyanodiphenylacrylate is water soluble, and also compatible with the other ingredients in the formulation. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below. When the cyanodiphenylacrylate is in the water soluble form, the aqueous phase thickening agent also contributes to stabilizing this ingredient in the composition and improving penetration into the stratum corneum.

1. Polysaccharides

Polysaccharides may be suitable aqueous phase thickening agents. Examples of such polysaccharides include naturally derived materials such as agar, agarose, *alicaligenes* polysaccharides, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

2. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

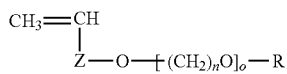

wherein Z is —$(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or CH$_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl(meth)acrylate, divinylbenzene, (poly) ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/C$_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CTFA names polyglycerin-20, polyglycerin-40, and the like.

D. Oil Phase Structuring Agents

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The oil phase structuring agent is compatible with the cyanodiphenylacrylate, particularly if the cyanodiphenylacrylate is soluble in the nonpolar oils forming the oil phase of the composition. The term "compatible" means that the oil phase structuring agent and cyanodiphenylacrylate derivative are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety. It is particularly desirable to incorporate silicone elastomers into the compositions of the invention because they provide excellent "feel" to the composition, are very stable in cosmetic formulations, and relatively inexpensive.

(b). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

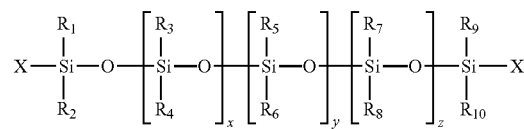

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(c). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

(d). Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

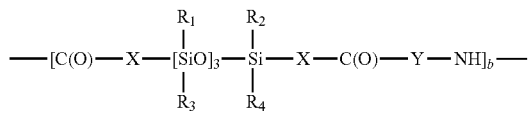

X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

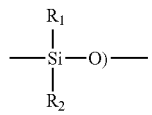

and Y is:
(a) a linear or branched alkylene having from about 1-40 carbon atoms which may be substituted with:
    (i) one or more amide groups having the general formula $R_1CONR_1$, or
    (ii) $C_{5-6}$ cyclic ring, or
    (iii) phenylene which may be substituted with one or more $C_{1-10}$ alkyl groups, or
    (iv) hydroxy, or
    (v) $C_{3-8}$ cycloalkane, or
    (vi) $C_{1-20}$ alkyl which may be substituted with one or more hydroxy groups, or
    (vii) $C_{1-10}$ alkyl amines; or
(b) $TR_5R_6R_7$
    wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

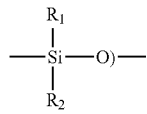

Preferred is where $R_1$, $R_2$, $R_3$, and $R_4$ are $C_{1-10}$, preferably methyl; and X and Y is a linear or branched alkylene. linear or branched alkylene. Preferred are silicone polyamides having the general formula:

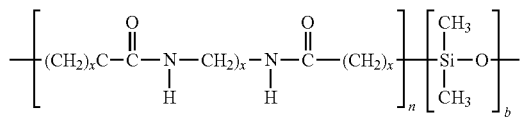

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether. Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

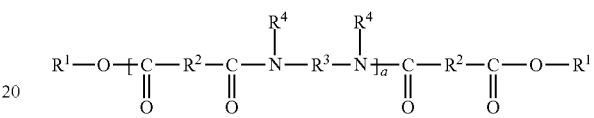

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

(e). Natural or Synthetic Organic Waxes

Also suitable as the oil phase structuring agent may be one or more natural or synthetic waxes such as animal, vegetable, or mineral waxes. Preferably such waxes will have a higher melting point such as from about 35 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, *citrus* wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and poly-alkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

(f). Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

(g). Silicas and Silicates

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

E. Organic Surfactants

The composition may contain one or more organic surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula:

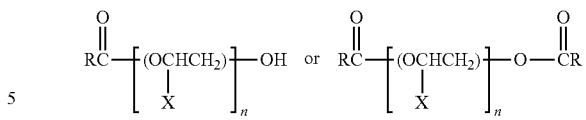

where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of poly-alkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Also suitable are phosphate based emulsifiers such as those which are $C_{2-40}$ alcohols and phosphoric acid. More preferred is where the alcohols are fatty C6-22 alcohols such as cetyl, stearyl, behenyl, alcohols or salts thereof. Also suitable are diesters phosphoric acid and one or more C2-40 alcohols, e.g. dicetyl phosphate; or fatty C6-30 ethoxylated alcohols and phosphoric acid, e.g. ceteth-10 phosphate, steareth-10 phosphate; C12-13 Pareth-2 Phosphate; Laureth-7 Phosphate; and the like.

Inulin based emulsifiers may also be used. Examples include inulin lauryl carbamate; palmitoyl inulin; sodium carboxymethyl inulin; stearoyl inulin; undecylenoyl inulin; and mixtures thereof.

It may also be desirable to incorporate various types of surfactants that induce the formation of liquid crystals in the composition. Examples of such surfactants include ceramide based surfactants such as phytosphingosines; C12-20 alkyl glucosides; coco glucosides; olive based semi-solids such as cetyl palmitate; sorbitan olivate; sorbitan palmitate; or phospholipid based emulsifiers such as lecithin, hydrogenated lecithin, phytosterols, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

F. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

G. Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, camelina sativa seed oil, *boswellia serrata* extract, olive extract, *Aribodopsis Thaliana* extract, *Acacia Dealbata* extract, *Acer Saccharinum* (sugar maple), acidopholus, acorns, aesculus, *Alicaligenes* polysaccharides, agaricus, agave, agrimonia, algae, aloe, *citrus, brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum*, Bifida Ferment lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea*, and mixtures thereof.

H. Sunscreens

It may also be desirable to include one or more sunscreens in the compositions of the invention. Such sunscreens include chemical UVA or UVB sunscreens or physical sunscreens in the particulate form. Inclusion of sunscreens in the compositions containing the cyanodiphenylacrylate will provide additional protection to skin during daylight hours and promote the effectiveness of the cyanodiphenylacrylate on the skin.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

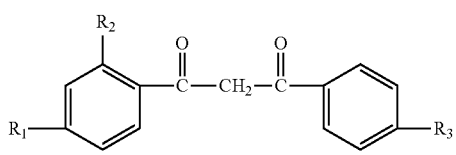

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene i dicamphor sulfonic acid, having the formula:

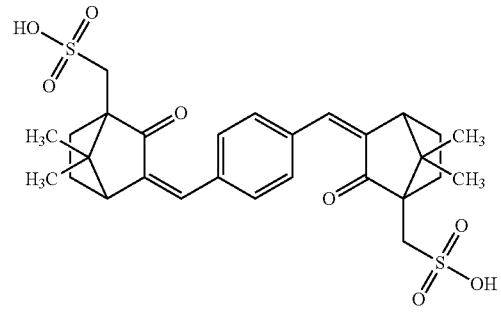 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

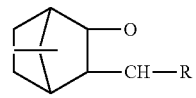

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

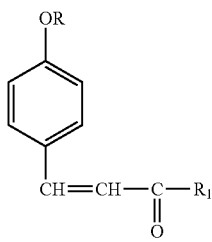

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

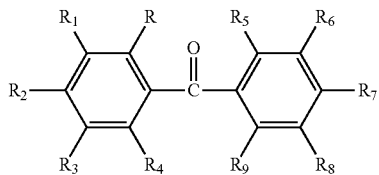

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

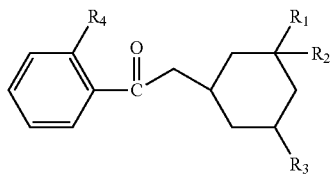

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomethyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

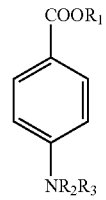

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof. Generally, the amount of the UVB chemical sunscreen present may range from about 0.001-45%, preferably 0.005-40%, more preferably about 0.01-35% by weight of the total composition.

Also suitable are certain esters of 2-phenyl ethanol and benzoic acid. One example is phenyethyl benzoate, which is sold under the tradename X-Tend 226®, by International Specialty Products.

If desired, the compositions of the invention may be formulated to have a certain SPF (sun protective factor) values ranging from about 1-50, preferably about 2-45, most preferably about 5-30. Calculation of SPF values is well known in the art.

I. Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmented powders. Suitable non-pigmented powders include zinc oxide or titanium dioxide (which may be micronized, e.g. having a particle size of from about 0.1 to 1 micron and are generally known for having SPF properties, particularly UVA), bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

J. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

K. Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, niacin, niacinamide, nicotinic acid, nicotinic acid dinucleotide, and so on, as well as coenzymes such as thiamine pyrophoshate, flavin adenine dinucleotide, folic acid, pyridoxal phosphate, tetrahydrofolic acid, and so on. Also Vitamin A and derivatives thereof are suitable. Examples are retinol palmitate, retinol, retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

L. Film Formers

It may be desirable to include one or more film forming ingredients in the cosmetic compositions of the invention. Suitable film formers are ingredients that contribute to formation of a film on the keratinous surface. In some cases the film formers may provide films that provide long wearing or transfer resistant properties such that the cosmetic applied to the keratinous surface will remain for periods of time ranging from 3 to 16 hours. If present, such film formers may range from about 0.01 to 50%, preferably from about 0.1 to 40%, more preferably from about 0.5 to 35% by weight of the total composition. The film formers are most often found in the polymeric form and may be natural or synthetic polymers. If synthetic, silicone polymers, organic polymers or copolymers of silicones and organic groups may be acceptable. Suitable film formers include, but are not limited to:

1. Silicone Resins

One particularly suitable type of silicone film former is a silicone resin. Silicone resins are generally highly crosslinked structures comprising combinations of M, D, T, and Q units. The term "M" means a monofunctional siloxy unit having the general formula:

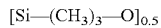

In cases where the M unit is other than methyl (such as ethyl, propyl, ethoxy, etc.) the M unit may have a prime after it, e.g. M'.

The term "D" means a difunctional siloxy unit having the general formula:

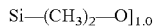

The difunctional unit may be substituted with alkyl groups other than methyl, such as ethyl, propyl, alkylene glycol, and the like, in which case the D unit may be referred to as D', with the prime indicating a substitution.

The term "T" means a trifunctional siloxy unit having the general formula:

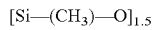

The trifunctional unit may be substituted with substituents other than methyl, in which case it may be referred to as T'.

The term "Q" refers to a quadrifunctional siloxy unit having the general formula:

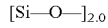

The silicone resins that may be used as film formers in the compositions of the invention preferably comprise highly crosslinked combinations of M, T, and Q units. Examples of such resins include trimethylsiloxysilicate which can be purchased from Dow Corning Corporation as 749 Fluid, or from GE Silicones under the SR-1000 tradename. Also suitable is a silicone resin that contains a large percentage of T groups, such as MK resin sold by Wacker-Chemie, having the CTFA name polymethylsilsesquioxane.

2. Copolymers of Silicone and Organic Monomers

Also suitable for use as the film formers are copolymers of silicone and organic monomers such as acrylates, methacrylates, and the like. Examples of such suitable film forming polymers include those commonly referred to as silicone acrylate or vinyl silicone copolymers, such as those sold by 3M under the brand name "Silicone Plus" polymers such as SA-70, having the CTFA name Polysilicone-7 and is a copolymer of isobutylmethacrylate and n-butyl endblocked polydimethylsiloxane propyl methacrylate; or VS-70 having the CTFA name Polysilicone-6, which is a copolymer of dimethylsiloxane and methyl-3 mercaptopropyl siloxane reacted with isobutyl methacrylate; or VS-80, having the CTFA name Polysilicone-8, which has the general structure:

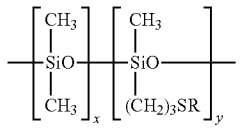

where R represents the acrylates copolymer radical.

3. Organic Polymers

Also suitable as film formers include various types of organic polymers such as polymers formed from acrylic acid, methacrylic acid, or their simple $C_{1-10}$ carboxylic acid esters, such as methyl methacrylate, methyl acrylate, and the like.

4. Natural Polymers

Also suitable are various types of natural polymers such as shellac, natural resins, chitin, and the like.

M. DNA Repair Enzymes

It may also be desirable to incorporate one or more DNA repair enzymes into the composition of the invention. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of a species of *micrococcus*), lecithin, and water. Photosomes® comprises a mixture of plankton extract (which is the extract of a biomass which includes enzymes from one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as Bifida lysate or Bifida ferment lysate, the latter a lysate from Bifido bacteria which contains the metabolic products and cytoplasmic fractions when Bifido bacteria are cultured, inactivated and then disintegrated. This material has the INCI name Bifida Ferment Lysate.

Other suitable DNA repair enzymes include Endonuclease V, which may be produced by the denV gene of the bacteriophage T4. Also suitable are T4 endonuclease; $O^6$-methylguanine-DNA methyltransferases; photolyases, base glycosylases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; polymerases; ligases; and topoisomerases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch excision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma Pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-1 or RAD-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog (REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

N. The Cosmetic Compositions

The compositions of the invention containing the cyanodiphenylacrylates may be found in a variety of forms, such as anhydrous compositions, aqueous based solutions, serums, gels, skin creams or lotions, or color cosmetic compositions such as foundation makeup, mascara, lip color, blush, eyeshadow, and the like. In the case where the composition is in the anhydrous form the cyanodiphenylacrylate may be solubilized or dispersed in the oil phase of the emulsion; or if the cyanodiphenylacrylate is water soluble it may be solvated in polar solvents, typically ingredients referred to as humectants such as glycerine or alkylene glycols prior to formation of an anhydrous emulsion. Preferably the cyanodiphenylacrylate is lipophilic and soluble in the oil or silicone phase of the composition.

Emulsions comprise from about 0.1 to 95%, preferably from about 1 to 90%, more preferably from about 2 to 85% water; and from about 0.1 to 95%, preferably from about 1 to 90%, more preferably from about 2 to 85% of one or more oils.

If the composition is in the emulsion form, the cyanodiphenylacrylate is preferably found in the oil phase of the emulsion, which oil phase may be silicones, organic oils, or a combination thereof. Certain other derivatives are lipophilic in nature and will more likely be found in the oil phase of the emulsion.

Suitable serums or gels will generally comprise from about 1-99% water, and optionally from about 0.001-30% of an aqueous phase thickening agent. The other ingredients mentioned herein may be present in the percentage ranges set forth. In the case where the cynaodiphenylacrylate is lipophilic it will be dispersed in the aqueous phase.

Typical skin creams or lotions comprise from about 5-98% water, 1-85% oil, and from about 0.1 to 20% of one or more surfactants. Preferably the surfactants are nonionic and may be in the form of oxyalkylenated organosiloxanes or organic nonionic surfactants.

Typical color cosmetic compositions such as foundations, blush, eyeshadow and the like will preferably contain from about 5-98% water, 1-85% oil, and from about 0.1 to 20% of one or more surfactants in addition to from about 0.1 to 65% of particulates that are pigments or a combination of pigments and powders.

Typical mascara compositions generally contain from about 5-98% water, 1-85% oil, and from about 0.1 to 20% surfactant in addition to natural or synthetic polymers that are film forming, such as aqueous dispersions of acrylic copolymers, aqueous dispersions of polyurethane, or silicone resins.

Preferred compositions of the invention comprise skin creams, lotions, foundations, or sun protective products. Generally such products will be aqueous based and contain cyanodiphenyl acrylate, water, at least one oxyalkylenated organosiloxane emulsifier, one or more silicone oils, one or more organic oils, and one or more particulate sunscreens having a particle size ranging from about 0.1 to 5 microns; and one or more humectants. More preferred is an SPF composition comprising:

from about 0.1 to 10% of the cyanodiphenylacrylate, preferably ethylhexylmethoxycrylene,
from about 1 to 90% water,
from about 0.1 to 40% of at least one volatile oil
from about 0.1 to 40% of at least one non-volatile oil
from about 0.1 to 60% of at least one particulate sunscreen
from about 0.1 to 40% of one or more humectants.

Even more preferred is a composition where the at least one volatile oil comprises a silicone having a viscosity in the range of from about 0.5 to 5 cst or a volatile paraffinic hydrocarbon; the at least one non-volatile oil component comprises at least one silicone oil and at least one organic oil; the at least one particulate sunscreen comprises zinc oxide having a particle size ranging from about 0.1 to 5 microns; and the at least one humectant comprises a $C_{2-4}$ alkylene glycol or glycerin.

An even more preferred embodiment is where the volatile silicone comprises methyl trimethicone, the volatile paraffinic hydrocarbon comprises isododecane; the non-volatile oil component comprises dimethicone or diethicone, and the organic oil an ester; the particulate sunscreen comprises zinc oxide having a particle size ranging from about 0.1 to 5 microns; and the at least one humectant comprises propylene glycol or butylene glycol.

The above composition preferably has an SPF of greater than 20, more preferably greater than 25, even more preferred greater than 35 or 40.

The invention will be further described in connection with the following examples which are set forth for the purposes of illustration only.

Example 1

A topical composition with SPF was prepared as follows:

| Ingredient | Wt % | |
|---|---|---|
| Water | QS | QS |
| Methyl trimethicone | 12.60 | 12.60 |
| Butylene glycol | 6.00 | 6.00 |
| Zinc oxide | 5.00 | 5.00 |
| Ethylhexylmethoxycrylene | 5.00 | 5.00 |
| C12-15 alkyl benzoate | 4.35 | 4.35 |
| Titanium dioxide | 3.88 | 3.1 |
| Dimethicone | 3.79 | 3.70 |
| Neopentylglycol diethylhexanoate | 3.46 | 3.46 |
| Beeswax | 3.00 | 3.00 |
| Polydiethylsiloxane | 3.00 | 3.00 |
| Dipentaerythrityl tripolyhydroxystearate | | 2.00 |
| Isododecane | 2.18 | |
| Glycerin | 2.00 | 2.00 |
| Lauryl PEG-9 polydimethylsiloxyethyl dimethicone | 2.00 | 2.00 |
| Ethyl macadamiate | 2.00 | 2.00 |
| Acrylic acid/acrylonitrogens copolymer | | 1.94 |
| Cetyl PEG/PPG 10/1 dimethicone | 1.00 | 1.00 |
| Magnesium sulfate | 1.00 | 1.00 |
| Phenoxyethanol | 0.80 | 0.83 |
| Dimethicone/dimethicone PEG/PPG 15 crosspolymer | 0.50 | 0.50 |
| Iron oxides | 0.49 | 0.49 |
| Caprylyl glycol | 0.49 | 0.49 |
| Hydrolyzed wheat protein/PVP crosspolymer | | 0.40 |
| Isostearic acid | 0.40 | 0.40 |
| Trisiloxane | | 0.36 |
| Trimethylsiloxysilicate | 0.33 | 0.33 |
| Acrylates copolymer | | 0.30 |
| Polyhydroxystearic acid | 0.25 | 0.25 |
| Xanthan gum | 0.25 | 0.25 |
| Dimethicone silylate | | 0.24 |
| Tocopheryl acetate | | 0.20 |
| Ascorbyl tocopheryl maleate | | 0.18 |
| Oryzanol | | 0.18 |
| Pantenthine | | 0.16 |
| Disteardimonium hectorite | 0.24 | |

| Ingredient | Wt % | |
|---|---|---|
| Alicaligenes polysaccharides | 0.20 | |
| Tocopheryl acetate | 0.20 | |
| Pantethine | 0.16 | |
| Dimethicone/vinyl dimethicone crosspolymer | 0.15 | 0.15 |
| Propylene carbonate | 0.09 | |
| Lecithin | 0.01 | 0.01 |
| Potassium sorbate | | 0.004 |
| Tocopherol | | 0.003 |

The compositions were prepared by combining the ingredients well and mixing to form an emulsion.

Example 2

An anhydrous product with SPF was prepared as follows:

| Ingredients | w/w % |
|---|---|
| Ethylhexyl methoxycinnamate | 7.50 |
| Polyethylene | 6.00 |
| Heptyl undecylenate | 6.00 |
| Ethylhexylmethoxycrylene | 6.00 |
| Bis-diglyeryl polyacyladipate-2 | 5.29 |
| Homosalate | 5.00 |
| Mica/Aluminum Dimyristate/triethoxcaprylylsilane/disodium stearoyl glutamate | 5.00 |
| Mica/methylmethacrylate crosspolymer | 5.00 |
| Ethylhexyl salicylate | 5.00 |
| Microcrystalline wax | 4.50 |
| Simmondsia Chinensis (jojoba) seed oil | 4.00 |
| Butyloctyl salicylate | 4.00 |
| Gclyeryl hydrogenated rosinate | 4.00 |
| Oleic/linoleic/linolenic polyglyceride | 4.00 |
| HDI/trimethylol hexyllactone crosspolymer/silica | 3.50 |
| Avobenzone | 3.00 |
| Polyglyceryl-2 triisostearate | 2.81 |
| Octocrylene | 2.79 |
| Synthetic wax/synthetic beeswax/stearic acid | 2.40 |
| Ethyl macadamiate | 2.00 |
| Butyrospermum parkii (Shea Butter) | 2.00 |
| Beeswax | 1.80 |
| Methyl glucose sesquistearate | 1.50 |
| Dipentaerythrityl hexahydroxystearate/hexastearate/hexarosinate | 1.49 |
| Tricaprylin | 1.31 |
| Glyceryl dilaurate | 1.00 |
| Mauritia Flexuosa fruit oil | 1.00 |
| VP/Eicosene | 1.00 |
| Isononyl isononanoate | 1.00 |
| Tocopheryl acetate | 0.10 |
| Pentaerythrityl tetra-di-T-butyle hydroxyhdryocinnamate | 0.01 |

Example 3

Skin treatment oil-in-water (1), and oil-in-water-in-silicone oil (2), creams may be prepared as follows:

| Ingredient | w/w % | |
|---|---|---|
| | 1 | 2 |
| Water | QS | QS |
| Hydroxyethyl urea | 0.50 | |
| Hyaluronic acid | 9.00 | 9.00 |
| Disodium EDTA | 0.12 | |
| Creatine | 0.05 | |
| Sucrose | 0.50 | |
| Caffeine | 0.20 | |
| Caprylyl glycol | 0.40 | 0.28 |
| Caprylic/capric triglyceride/cetyl alcohol/C12-20 acid PEG-8 ester | 4.00 | |
| PEG-100 stearate | 1.20 | |
| C12-20 acid PEG-8 ester | 4.96 | |
| Caprylic/capric triglyceride | 0.55 | |
| Behenyl alcohol | 0.50 | |
| Coco caprylate caprate | 5.10 | |
| Sweet almond oil | 0.10 | |
| Dimethicone, 100 cst. | 2.50 | |
| Ethylhexylmethoxycrylene | 2.00 | 2.00 |
| Dimethicone, 6 cst | | 5.00 |
| Dimethicone (silicone gum/20 cst dimethicone blend) | | 8.00 |
| Dimethicone/polysilicone 11 | | 6.00 |
| Dimethicone/dimethicone PEG-10/15 crosspolymer | | 1.00 |
| Lauryl PEG-9 polydimethylsiloxyethyl dimethicone | | 1.00 |
| Sesame oil | 0.10 | |
| Potassium cetyl phosphate | 0.50 | |
| Apricot kernel oil | 0.10 | |
| Wheat bran extract/olive extract | 0.20 | 0.20 |
| Cholesterol | 0.20 | |
| Linoleic acid | 0.20 | |
| Cholesterol/potassium sulfate | 0.20 | |
| Theobroma grandiflorum seed butter | 1.40 | |
| Lauryl PCA | 0.01 | 1.00 |
| Dimethicone | 1.50 | |
| Phenoxyethanol | 0.70 | 0.60 |
| Water/polyaminopropyl biguanide | 0.40 | |
| Glycerin | 2.00 | |
| Butylene glycol | 1.00 | |
| Hexylene glycol | | 0.05 |
| Mica/titanium dioxide | 1.00 | 0.75 |
| Mica/titanium dioxide/triethoxycaprylyl silane | | 0.50 |
| Pearl powder | 0.001 | |
| Silica | 0.50 | |
| 30% aqueous sodium hydroxide | 0.35 | |
| Trehalose | 0.50 | |
| N-acetyl glucosamine | 1.00 | 1.00 |
| Water/purified Aribodopsis Thaliana extract/lecithin | 0.50 | 1.00 |
| Aqueous solution acetyl hexapeptide-8 | 1.00 | 1.00 |
| Yeast ferment extract | 1.00 | 1.00 |
| Water/lecithin/micrococcus lysate | 0.50 | 0.50 |
| Milk protein/lactose/glucose/fructose | 0.50 | 0.50 |
| Saccharide isomerate | 0.50 | |
| Whey protein | 0.50 | 0.560 |
| Water/butylene glycol/lecithin/lauryldimonium hydroxypropyl hydrolyzed soy protein/lecithin/xanthan gum/ascorbyl tocopheryl maleate | 1.00 | 1.00 |
| Glycerin/Padina Pavonica extract | 0.10 | 0.10 |
| Thermus Thermophillus ferment/glycerin | 0.05 | |
| Camelina Sativa seed oil | 0.05 | |
| Water/gold/hydrolyzed wheat protein | 0.001 | |
| Sorbitol/water/ascophyllum nodosum extract/asparagopsis armata extract | 0.25 | |
| Butylene glycol | 0.50 | |
| Boswellia Serrata extract | 0.05 | |
| Calophyllum Inophyllum (tamanu) seed oil | 0.05 | |
| Fragrance | 0.20 | |
| FD&C yellow No. 5 (1% aqueous solution) | 0.05 | |
| Aminomethyl propanol | | 0.03 |
| Sodim phosphate dibasic (10% aqueous solution) | | 0.75 |
| Citric acid (10% aqueous solution) | | 0.008 |
| Sodium acrylate/sodium acryloyldimethyl taurate copolymer/hydrogenated polydecene/laureth-8 | 1.00 | 1.00 |
| Ammonium acrylodimethyltaurate/VP copolymer | | 0.70 |
| Water/butylene glycol/decarboxy carnosine HCl | | 0.50 |
| Dimethyltolyl propylresorcinol | 0.50 | |

The composition is prepared by combining the water phase and oil phase ingredients separately, then emulsifying to form an emulsion.

Example 4

A water in silicone oil emulsion skin serum is prepared as follows:

| Ingredient | w/w % |
|---|---|
| Dimethicone/dimethicone PEG-10/15 crosspolymer | 4.00 |
| Dimethicone/dimethiconol | 1.00 |
| Dimethicone, 6 cst. | 6.00 |
| Trisiloxane (1.0 cst) | 16.00 |
| Water | QS |
| Phenoxyethanol | 0.50 |
| Caprylyl glycol/phenoxyethanol/hexylene glycol/iodopropynyl butylcarbamate | 0.50 |
| Water/polyaminobiguanide | 0.20 |
| Butylene glycol | 2.00 |
| Ethylhexylmethoxycrylene | 1.00 |
| Glycerin | 10.00 |
| Sodium citrate | 0.50 |

The composition is prepared by combining the oil phase ingredients and water phase ingredients separately, then mixing well to emulsify.

Example 5

Oil-in-water (O/W) and water-in-oil (W/O) emulsion mascaras are prepared as follows:

| | w/w % | |
|---|---|---|
| Ingredient | O/W | W/O |
| Ethylenediamine/Stearyl Dimer Tallate Copolymer - Uniclear 100VG, Arizona Chemical | 10. | 12.00 |
| PEG-30 Dipolyhydroxystearate | — | 3.00 |
| Sorbitan tristearate | 1.00 | — |
| Glyceryl stearate/PEG-100 stearate | 1.00 | — |
| Stearic acid | 4.00 | 3.00 |
| Cetyl acetate/Acetylated lanolin alcohol | — | 1.00 |
| Dioctyl adipate/octyl stearate/octyl palmitate | 1.00 | — |
| Stearamide MEA stearate | 3.00 | — |
| Glyceryl olivate | — | 0.50 |
| Dioctyl malate | — | 1.00 |
| Dimethicone | 2.50 | — |
| Cyclomethicone | 5.00 | — |
| Isododecane | 11.00 | 38.00 |
| Ethanol | 0.50 | — |
| Water | QS | QS |
| Silica | 1.00 | — |
| Polysorbate 20 | 2.00 | — |
| *Acacia* gum | 0.25 | — |
| Ethylhexyl methoxycrylene | 0.50 | 0.50 |
| Dimethicone/dimethicone PEG/PPG 15 crosspolymer | 0.50 | 0.50 |
| Black iron oxide | 8.00 | 10.00 |
| Polyvinylpyrrolidone | 1.00 | — |
| Shellac | 2.00 | — |
| Acrylic copolymer solids dispersed in aqueous solution | 5.00 | 7.00 |
| Preservatives | 0.80 | — |

The mascaras are made by combining the oily phase ingredients except for the cyclomethicone and dimethicone and heating to about 90° C. until solids melt. The cyclomethicone and dimethicone are added to the mixture and the heat maintained at about 60° C. The water phase ingredients are combined and heated to about 60° C. and combined with the mixture. The phases are emulsified to form the final mixture.

Example 6

Emulsion foundation makeup compositions are prepared as follows:

| Ingredient | w/w % |
|---|---|
| Cyclomethicone | 16.90 |
| Polysilicone-11 | 5.00 |
| Cyclomethicone/dimethiconol | 1.00 |
| Dimethicone copolyol | 1.50 |
| Sorbitan sesquioleate | 1.50 |
| Phenyl trimethicone | 10.00 |
| Dimethicone | 10.00 |
| Red Iron Oxide treated with methicone | 0.50 |
| Yellow iron oxide treated with methicone | 1.22 |
| Black iron oxide treated with methicone | 0.13 |
| Titanium dioxide coated with methicone | 8.06 |
| Water | QS |
| Butylene glycol | 5.00 |
| Ethylhexylmethoxycrylene | 3.00 |
| Xanthan gum | 0.10 |
| Magnesium sulfate | 1.00 |
| Laureth-7 | 0.25 |

The water, oil and pigment phases are separately prepared by low shear mixing. The phases are combined with high shear blending to form a foundation makeup composition.

Example 7

Anhydrous emulsion skin treatment serums and gels may be prepared as follows:

| | w/w % | | |
|---|---|---|---|
| Ingredient | A | B | C |
| *Pinus Pinaster* bark extract | 0.50 | | |
| *Santalum Album* (sandalwood) extract/*phellodendron amurense* bark extract | | | 6.00 |
| Calcium carbonate/*Zea Mays* (corn) starch/*Glycine Soja* (soybean) extract | 0.5 | | |
| Lauroyl lysine | | | 8.00 |
| Butylene glycol | 7.00 | 7.00 | 2.00 |
| Ferulic acid | 0.10 | | |
| Glycerin | 10.00 | 10.00 | |
| PEG-8 | | | 1.00 |
| Polysorbate-80 | | | 0.50 |
| Dicarylyl carbonate | | | 22.00 |
| PEG-60 hydrogenated castor oil | | | 1.00 |
| *Simmondsia Chinensis* (jojoba) seed oil | | | 21.50 |
| Isopropyl isostearate | | | 5.00 |
| Isononyl isononanoate/ethylhexyl isononanoate | | | 17.00 |
| Dextrin palmitate | | | 7.00 |
| Glyceryl behenate/eicosadioate | | | 0.50 |
| Hinokitiol | 0.10 | | |
| PEG-10 dimethicone | 2.00 | 2.00 | |
| Dimethicone/caprylyl methicone/phenyl methicone | | 65.00 | |
| Silica | | | 7.50 |
| Nordihydroguaiaretic acid | 0.50 | | |
| *Camellia sinensis* (green tea) extract | 2.00 | | |
| Phenoxyethanol | 0.20 | 0.20 | 0.50 |
| Ethylhexylmethoxycrylene | 0.50 | 1.00 | 1.50 |
| Cyclomethicone/dimethicone/C30-45 olefin/phenyl methicone | 2.00 | | |
| Methyl trimethicone | 3.00 | 3.00 | |
| *Citrus grandis* (grapefruit) peel extract | 0.20 | | |
| Dimethicone/vinyl dimethicone cross polymer/methyl trimethicone | 71.40 | 75.30 | |

The compositions were prepared by combining the cyanodiphenylacrylate and glycerin. The remaining ingredients were combined and mixed well, followed by addition of the cyanodiphenylacrylate in glycerin.

Example 8

A foundation makeup is prepared as follows:

| Ingredient | w/w % |
| --- | --- |
| Cetyl PEG/PPG-10/1 dimethicone/polyglyceryl-4 isostearate/hexyl laurate | 1.00 |
| Red iron oxide/methicone | 0.60 |
| Yellow iron oxide | 1.47 |
| Dimethicone crosspolymer-3/isododecane | 22.00 |
| Polyethylene | 4.00 |
| Mica | 10.37 |
| Trifluoromethyl C1-4 alkyl dimethicone/cyclomehticone/propylene carbonate | 6.00 |
| Titanium dioxide/methicone | 6.80 |
| Silica | 0.001 |
| Ethylhexylmethoxycrylene | 1.00 |
| Cyclopentasiloxane | QS |
| Phenyl trimethicone | 3.80 |
| Dimethicone gum | 0.20 |
| Cyclomethicone/dimethicone/phenyl methicone | 28.10 |
| Mica/methyl methacrylate crosspolymer | 1.00 |
| Iron oxides/methicone | 0.20 |
| Titanium dioxide/iron oxides | 0.01 |
| Acrylates copolymer/diphenyl carbomethoxy acetoxy naphthopyran | 0.02 |
| Titanium dioxide/trimyristin/hydrogenated lecithin | 3.50 |

The composition was prepared by grinding the pigments in a portion of the oil. The remaining ingredient were combined with heat and mixed well, incorporating the pigment grind into the composition. The composition was a semi-solid beige colored composition suitable for use as a foundation.

Example 9

A lipstick composition is prepared as follows:

| Ingredient | w/w % |
| --- | --- |
| *Aloe barbadensis* extract/mineral oil | 0.50 |
| Trimethylsiloxypheny dimethicone (PDM 1000) | 1.00 |
| Octyldodecyl stearoyl stearate | 3.05 |
| Ceresin wax | 6.50 |
| Petrolatum | 32.05 |
| Hydrogenated vegetable oils | 14.00 |
| Polybutene | 0.25 |
| Ozokerite | 16.25 |
| Ethylhexyl methoxycinnamate | 7.50 |
| Propyl paraben | 0.15 |
| Phenyl trimethicone | 1.00 |
| Bis-diglyceryl polyacyladipate | 2.50 |
| Ethylhexylmethoxycrylene | 1.00 |
| Cetyl esters | QS |
| Ethylhexyl salicylate | 3.50 |
| Dimethicone/dimethicone PEG/PPG 15 crosspolymer | 1.00 |
| Tocopheryl acetate | 0.25 |

The composition is prepared by grinding the pigments in a portion of the cetyl esters. The waxes and oils were separately combined with heat and mixed well. The pigment grind was added to the mixture and stirred well. The mixture is poured into molds and allowed to cool to room temperature.

Example 10

Powder eyeshadow and blush compositions are prepared as follows

| Ingredient | Shadow w/w % | Blush w/w % |
| --- | --- | --- |
| Aluminum hydroxide | 0.003 | |
| Sorbitan sesquioleate | 0.001 | |
| Ascorbyl palmitate | 0.04 | |
| Barium sulfate | 0.0005 | |
| Soybean extract | 2.47 | |
| BHT | 0.70 | 0.05 |
| Lecithin | | 0.0004 |
| Candelilla wax | 5.85 | |
| Carnauba | 1.76 | |
| Castor seed oil | QS | |
| Polyglyceryl-3 beeswax | 3.23 | |
| Simethicone | | 0.05 |
| Dipentaerythrityl hexahydroxystearate | 2.50 | |
| Isodecyl neopentanoate | 0.05 | |
| Caprylic/capric triglycerides | 9.90 | |
| Mica | 4.75 | |
| Oleyl oleate | 6.70 | |
| Octyl palmitate | | 7.00 |
| Polybutene | | QS |
| Hydrogenated polyisobutene | | 30.13 |
| Dextrin palmitate | | 11.00 |
| Ozokerite | 2.35 | |
| Synthetic wax | 4.95 | |
| Diisostearyl malate | 8.70 | |
| Bis-diglyceryl polyacyladipate-2 | 1.47 | |
| Polydecene | 2.10 | 0.35 |
| Mica/titanium dioxide | | 0.80 |
| Propyl paraben | | 0.10 |
| Titanium dioxide | 3.10 | |
| Tocopheryl acetate | 0.04 | |
| Iron oxides | 5.11 | |
| FD&C blue no. 1 aluminum lake | 0.10 | 0.002 |
| Dimethicone/dimethicone PEG/PPG 15 crosspolymer | 1.00 | 1.00 |
| D&C Red No. 6 | | 0.01 |
| D&C Red No. 7 Calcium Lake | 0.36 | 0.25 |
| Fragrance | | 0.50 |
| Ethylhexylmethoxycrylene | 0.80 | 0.80 |

The compositions are prepared by grinding the pigments in a portion of the oil. Separately, the oils and waxes were combined with heat and mixed well. The pigment grind is added. The compositions are pressed into pans.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claimed is:

1. A topical composition comprising at least one α-cyanodiphenylacrylate and dimethicone silylate present in an amount sufficient to increase blocking of UVA light when compared to the same composition not containing dimethicone silylate.

2. The composition of claim 1 further comprising an organosiloxane emulsifier.

3. The composition of claim 1 wherein the α-cyanodiphenylacrylate has the general formula:

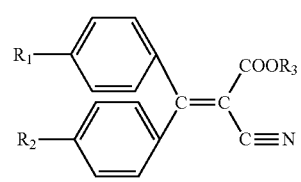

wherein $R_1$ and $R_2$ are each independently straight or branched chain $C_{1-30}$ alkoxy; any non-alkoxy $R_1$ or $R_2$ radical is hydrogen; and $R_3$ is a straight or branched chain $C_{1-30}$ alkyl.

4. The composition of claim 3 wherein $R_1$ and $R_2$ are each independently $C_{1-8}$ alkoxy, and any non-alkoxy radical $R_1$ or $R_2$ is hydrogen; and $R_3$ is a straight or branched chain $C_{2-20}$ alkyl.

5. The composition of claim 4 wherein R1 and R2 are each independently methoxy, and any non-methoxy $R_1$ or $R_2$ is hydrogen; and $R_3$ is a $C_{2-20}$ alkyl.

6. The composition of claim 1 wherein the α-cyanodiphenylacrylate is ethylhexylmethoxycrylene.

7. The composition of claim 2 wherein the oxyalklenated organosiloxane emulsifier has the general formula:

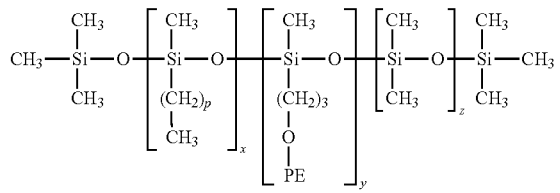

wherein p is 0-40, PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously, and z are each independently 0 to 1,000,000.

8. The composition of claim 7 wherein p is 0, a is 1 to 15, and b is 0 to 10.

9. The composition of claim 8 wherein p is 0, a is 10 and b is 1.

10. The composition of claim 6 further comprising an oxyalkylenated organosiloxane emulsifier that is Lauryl PEG-9 polydimethylsiloxy ethyl dimethicone.

11. The composition of claim 2 wherein the oxyalkylenated organosiloxane emulsifier is crosslinked.

12. The composition of claim 11 wherein the crosslinked emulsifier is selected from the group consisting of Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; PEG-15 Laurylpolydimethylsiloxyethyl Crosspolymer; and mixtures thereof.

13. The composition of claim 12 wherein the crosslinked emulsifier comprises Dimethicone/Dimethicone PEG/PPG-15 Crosspolymer.

14. The composition of claim 1 further comprising at least one particulate sunscreen having a particle size ranging from about 0.1 to 5 microns.

15. The composition of claim 14 wherein the particulate sunscreen comprises zinc oxide.

16. The composition of claim 14 additionally comprising at least one DNA repair enzyme.

17. The composition of claim 14 additionally comprising glycerin or a C2-4 alkylene glycol.

18. The composition of claim 14 additionally comprising methyl trimethicone.

* * * * *